United States Patent [19]
Uwajima et al.

[11] Patent Number: 4,666,842
[45] Date of Patent: May 19, 1987

[54] NOVEL ALDEHYDE OXIDASE AND PROCESS FOR PRODUCING SAME

[75] Inventors: Takayuki Uwajima; Kinya Fujishiro, both of Machida; Kenichiro Takayama, Atsugi, all of Japan

[73] Assignee: Kyowa Hakko Kogyo Co., Inc., Tokyo, Japan

[21] Appl. No.: 816,986

[22] Filed: Jan. 9, 1986

Related U.S. Application Data

[63] Continuation of Ser. No. 716,514, Mar. 26, 1985, abandoned, which is a continuation of Ser. No. 482,890, Apr. 7, 1983, abandoned.

[30] Foreign Application Priority Data

Apr. 12, 1982 [JP] Japan .................. 57-60709

[51] Int. Cl.$^4$ .................. C12N 9/02; C12N 1/20; C12R 1/38
[52] U.S. Cl. .................. 435/189; 435/253; 435/874
[58] Field of Search .................. 435/189, 253

[56] References Cited

PUBLICATIONS

R. Savini, Chemical Abstracts, Col. 47, No. 15, column 7582, reference b 8-10-53, "Oxidation of Aldehydes by Microorganisms".

J. Kurth et al., Chemical Abstracts, vol. 90, No. 7, p. 232, Abstract No. 50467 m 2-12-79, "Transformation of aliphatic aldehydes . . .".

A. Ando, Chemical Abstracts, vol. 67, No. 13, p. 5732, Abstract No. 61139 g 9-25-67, "Purification and Properties . . .".

R. Numazawa, Chemical Abstracts, vol. 82, No. 9, p. 198, Abstract No. 53235 e, 3-3-75, "Microbial Degradation of formaldehyde . . .".

V. F. Kazimirova et al., Chemical Abstracts, vol. 51, No. 1, Columns 11460-11461, reference i, a, 1-10-60, "Oxidative changes of aldehydes . . .".

T. Fugii et al., Chemical Abstracts, vol. 81, No. 21, p. 109, Abstract No. 532051 z, 11-25-74, "Oxygen-dependent oxidation . . .".

*Primary Examiner*—Lionel M. Shapiro
*Attorney, Agent, or Firm*—Fitzpatrick, Cella, Harper & Scinto

[57] ABSTRACT

Disclosed is a new enzyme, aldehyde oxidase, which catalyzes the oxidation of an aldehyde to a corresponding acid but does not have any catalytic action upon other substrates. Also disclosed is a fermentative process from producing the enzyme.

6 Claims, 4 Drawing Figures

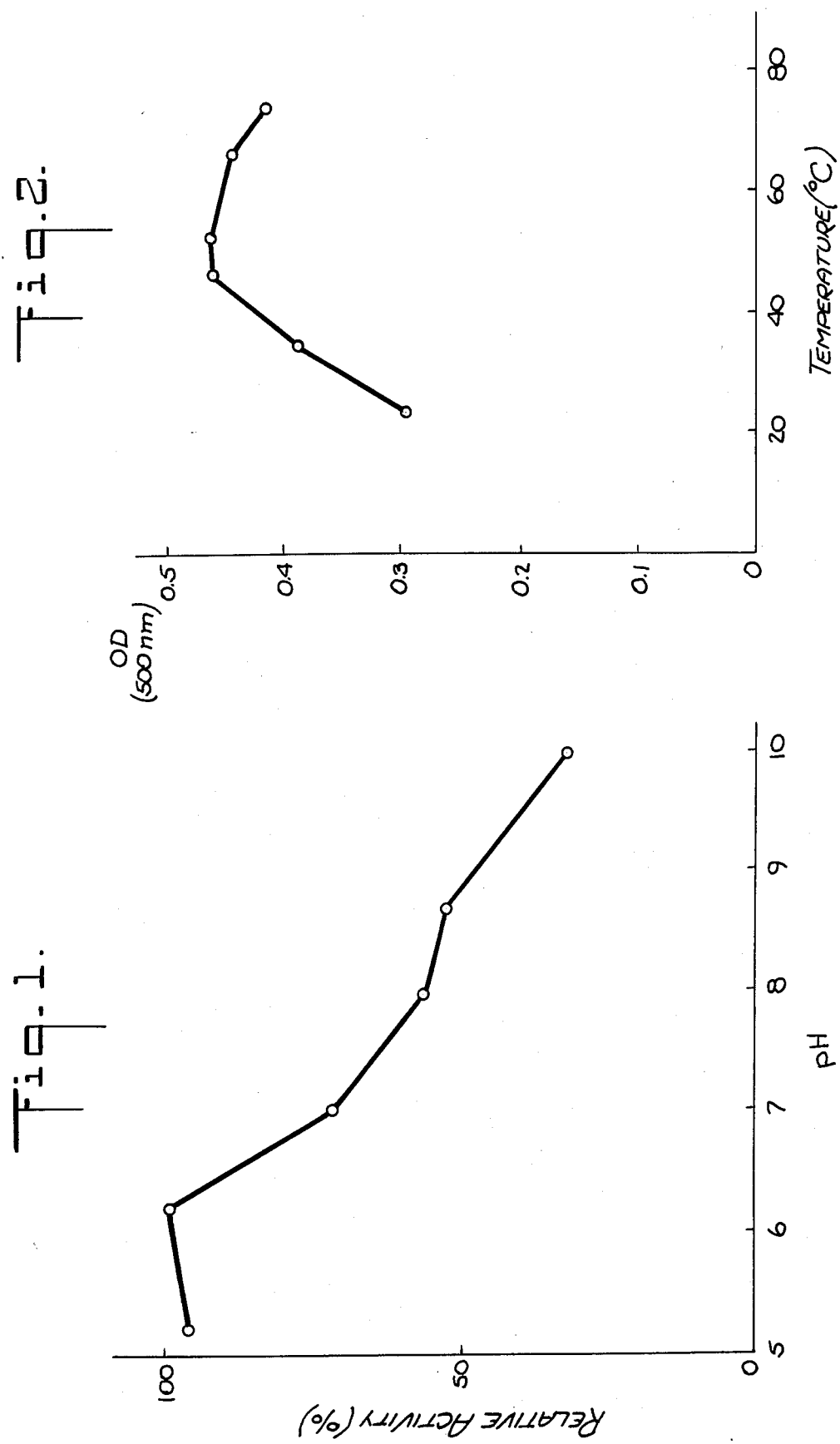

NOVEL ALDEHYDE OXIDASE AND PROCESS FOR PRODUCING SAME

This application is a continuation of application Ser. No. 716,514, filed Mar. 26, 1985, now abandoned, which is a continuation of application Ser. No. 482,890, filed on Apr. 7, 1983, both now abandoned.

BACKGROUND OF THE INVENTION

The present invention relates to a novel aldehyde oxidase and, more particularly, to an aldehyde oxidase which catalyzes the oxidation reaction of a substrate aldehyde to the corresponding acid but does not have any catalytic action upon nitrogen-containing aromatic heterocyclic compounds, purine, hypoxanthine and quinine. The invention also pertains to a microbial process for producing this enzyme.

Aldehyde oxidase (EC 1.2.3.1) has heretofore been derived from animal liver such as that of pigs, rabbits, etc., and is known to catalyze the reaction represented by the following equation (1):

$$RCHO + O_2 + H_2O \rightarrow RCOOH + H_2O_2 \quad (1)$$

Aldehyde oxidase of animal origin acts not only upon an aldehyde, but also upon a wide spectrum of various nitrogen-containing aromatic heterocyclic compounds, purine, hypoxanthine, quinines, etc. [J. Biol. Chem., 237, 922(1962), J. Biol. Chem., 239, 2022(1964); J. Biol. Chem., 239, 2027(1964)]. Therefore, it has been reported that those enzymes which have an aldehyde oxidase activity, a quinine oxidase activity and an N'-methylnicotineamide oxidase activity are one and the same protein [J. Biol. Chem., 237, 922(1962)].

Because of the lack of specific substrate activity, use of the known aldehyde oxidase for various purposes has been severly restricted. Accordingly, for commercial application, a need exists for an enzyme which does not suffer from the aforementioned drawback. To this end, it has now been found that certain microorganisms are capable of producing a novel aldehyde oxidase having a different substrate specifically than that of the heretofore known aldehyde oxidase.

SUMMARY OF THE INVENTION

In accordance with the present invention, aldehyde oxidase which is characterized by catalyzing the oxidation of an aldehyde to the corresponding acid but does not have any substrate specificity to nitrogen-containing aromatic heterocyclic compounds, purine, hypoxanthine and quinine, is produced by culturing a microorganism belonging to the genus Pseudomonas, Bacillus, Microbacteruim, Escherichia, Bdellovibrio, Cytophaga or Sporolactobacillus and which is capable of producing said enzyme, in a nutrient medium until recoverable quantities of the enzyme is produced, and thereafter recovering the enzyme therefrom.

The composition of matter aspect of the invention pertains to the enzyme, aldehyde oxidase, which is characterized by catalyzing the oxidation of an aldehyde to the corresponding acid and an absence of substrate specificity to nitrogen-containing aromatic heterocyclic compounds, purine, hypoxanthine and quinine.

The enzyme of the present invention is thus useful as a reagent for the quantative determination of various aldehydes in the field of clinical diagnosis and also to deodorize the odor of soybean etc. in the food industry field.

BRIEF DESCRIPTION OF THE DRAWINGS

The present invention is further illustrated in the accompanying drawings wherein:

FIG. 1 is a plot of the activity of the enzyme of the invention at various pHs;

FIG. 2 is a plot of the activity of the enzyme of the invention at various temperatures at a pH 7.0;

DESCRIPTION OF THE INVENTION

Figure 4:
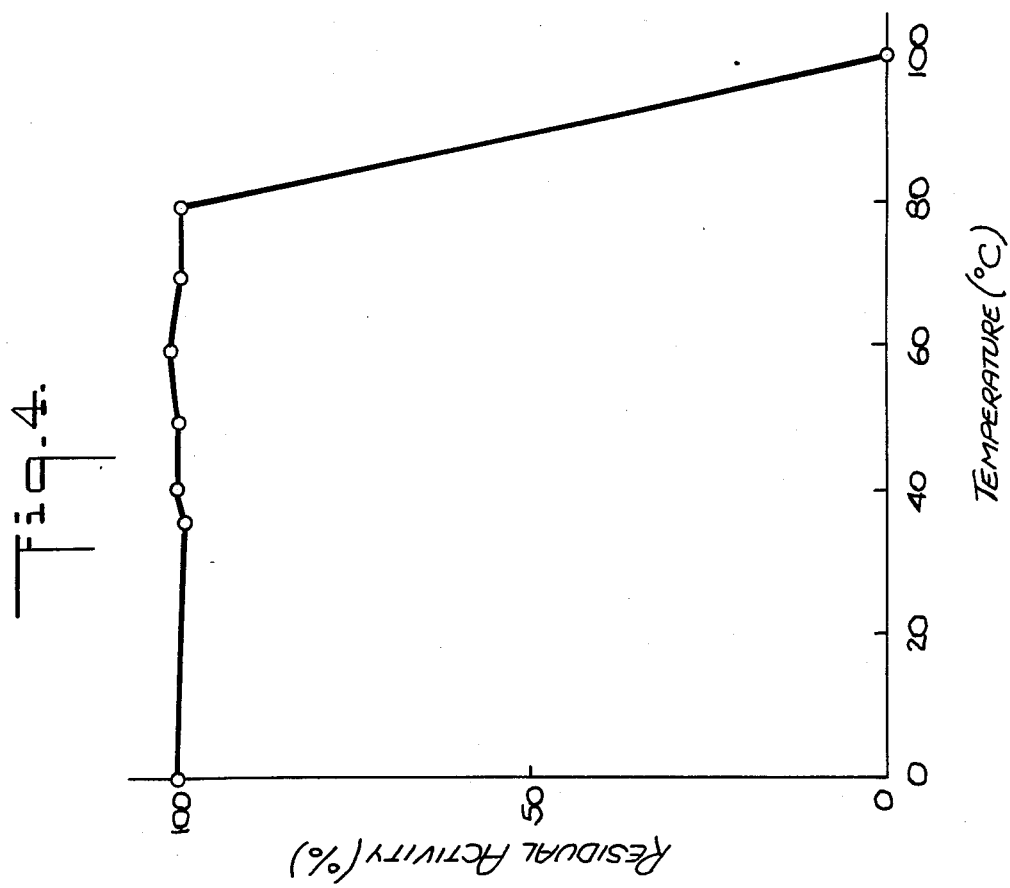
FIG. 4 is a plot of the temperature stability at pH 7.0 of the enzyme of the invention.
Figure 3:
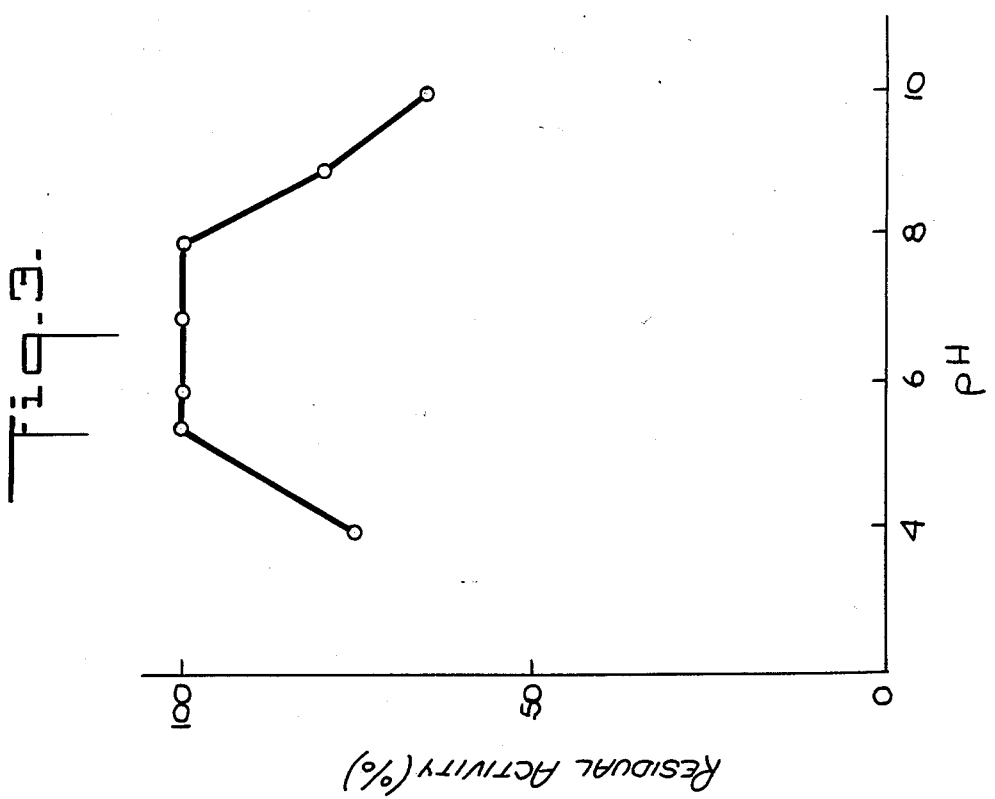
FIG. 3 is a plot of the pH stability of the enzyme of the invention after treatment of 70° C. for 30 minutes.

The properties of the aldehyde oxidase of the present invention are determined by the following procedures.

I. Procedure for determining enzyme titer

The amount of enzyme for decomposing 1 μmol of acetaldehyde in the presence of oxygen at 37° C. in one minute is designated as one unit. Specific activity is expressed by unit per mg of protein. The amount of enzyme protein is measured according to the method of O. H. Lowry, N. J. Rosebrough, A. L. Farr and R. J. Randall, J. Biol. Chem., 193 265(1951) using a copper-Folin reagent.

(a) Principle

The enzyme activity can be measured by allowing the hydrogen peroxide formed from acetaldehyde by the action of the enzyme to react with 4-aminoantipyrine and phenol in the presence of a peroxidase and by quantitatively determining the amount of quinoneimine formed. The reaction is illustrated by the following equations (1) and (2):

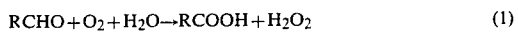

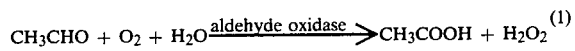

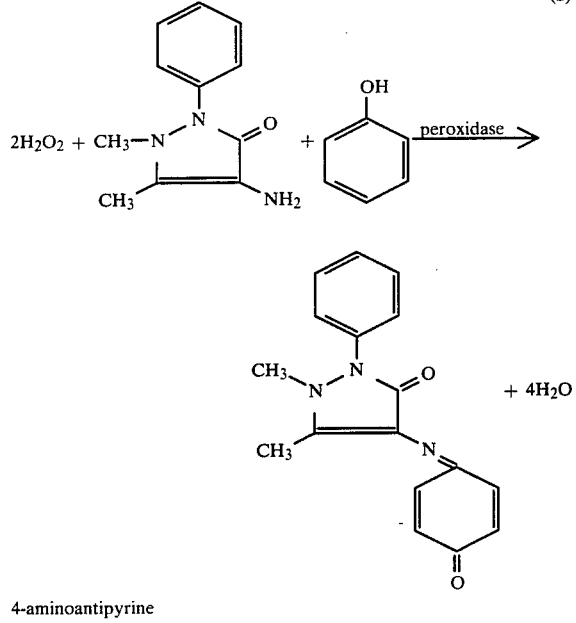

4-aminoantipyrine

The principle of the reaction according to equation (2) is given in C. C. Allain, et al.: Clin, Chem., 20, 470(1974).

(b) Reagents

| (1) Substrate: | 0.1 M acetaldehyde | 0.5 ml |
|---|---|---|
| (2) Buffer solution: | 0.1 M phosphate buffer solution (containing disodium phosphate and monosodium phosphate) (pH 7) | 1.0 ml |
| (3) 4-aminoantipyrine: | 2.4 mM aqueous solution | 0.5 ml |
| (4) Phenol: | 42 mM aqueous solution | 0.5 ml |
| (5) Peroxidase aqueous solution: | (protein: 2 mg/ml, specific activity: 100) | 0.1 ml |
| (6) Water: | | 0.3 ml |
| (7) Enzyme aqueous solution | | 0.1 ml |

(c) Procedure

The above reagents (1)-(6) are put into a test tube, thoroughly shaken, and left standing at 37° C. for 5 minutes. Then, the enzyme solution (7) is added to the test tube to make up a total volume of 3 ml, and the test tube is shaken at 37° C. for 10 minutes to complete the reaction. As a control, the procedure is repeated using water in place of the substrate. The absorbancies of the reaction solution and control at 500 nm are measured, and the difference between the absorbancies is obtained as ΔO.D.

(d) Calculation of titer

One unit of aldehyde oxidase is the amount of enzyme for decomposing 1 μmole of acetaldehyde at 37° C. in one minute. The absorbancy coefficient of 1 mM quinoneimine is reported in Clin. Chem., 20, 470(1974) to be 5.33. Therefore, if the absorbancy (ΔO.D.) of 3 ml of the reaction solution at 500 nm as obtained in the procedure (C) is designation as a, titer (A) per ml of the enzyme solution can be given as follows:

$$A = \underline{a} \times \frac{1}{5.33} \times 3 \times \frac{1}{10}$$

$$= \underline{a} \times 0.56 \text{ (unit/ml)}$$

II. Physical and chemical properties of the aldehyde oxidase of the present invention are described below (hereinafter, the aldehyde oxidase will be sometimes referred to merely as "the present enzyme"). A purified enzyme prepared in Example 1 is used as the aldehyde oxidase.

(1) Activity and substrate specificity

The present enzyme catalyzes the oxidation reaction according to equation (1) to produce an acid corresponding to a substrate aldehyde:

$$RCHO + O_2 + H_2O \rightarrow RCOOH + H_2O_2 \quad (1)$$

For example, formaldehyde, acetaldehyde and glyceraldehyde are oxidized to formic acid, acetic acid and glyceric acid respectively. The present enzyme acts upon a wide range of aldehydes, for example, saturated aliphatic aldehydes such as formaldehyde, acetaldehyde, propionaldehyde, n-valeraldehyde, n-hexylaldehyde, heptylaldehyde, etc.; unsaturated aliphatic aldehydes such as crotonaldehyde, citral, etc.; aromatic aldehydes such as benzaldehyde, etc.; D- or L-glyceraldehyde, etc. On the other hand, the present enzyme does not act upon alcohols such as methanol, ethanol, etc., N'-methylnicotineamide, quinoline, quinine, and the like.

In the following Table 1, the relative activity of the present enzyme upon various substrates is set forth.

TABLE 1

| Substrate specificity | |
|---|---|
| Substrate | Relative activity |
| Formaldehyde | 100% |
| Acetaldehyde | 266 |
| Propionaldehyde | 285 |
| n-Valeraldehyde | 367 |
| n-Hexylaldehyde | 390 |
| Heptylaldehyde | 387 |
| Crotonaldehyde | 260 |
| Citral | 291 |
| Benzaldehyde | 93 |
| D-Glyceraldehyde | 270 |
| L-Glyceraldehyde | 23 |
| Methanol | 0 |
| Ethanol | 0 |
| N'—Methylnicotinamide | 0 |
| Quinoline | 0 |
| Quinine | 0 |
| Purine | 0 |
| Hypoxanthine | 0 |

(2) Optimum pH and temperature, and stable pH and temperature ranges

The optimum pH of the present enzyme is about 6.5. The present enzyme is stable at a pH range of 5.5–8 when treated at 70° C. for 30 minutes. The optimum temperature of the present enzyme is about 50° C., and it is stable up to 80° C. when treated at pH 7.0 for 30 minutes. See also the acompanying drawing figures.

(3) Influence of various metal ions and inhibitors

The present enzyme is inhibited by mercuric chloride and p-chloromercuriphenylsulfonic acid, and thus it appears that an SH group takes part in the reaction. The influence of various metal ions and inhibitors upon the present enzyme is shown in Table 2.

TABLE 2

| Influence of various metal ions and inhibitors | | |
|---|---|---|
| | Concentration (mM) | Relative activity (%) |
| None | 0 | 100 |
| Ca(CH$_3$COO)$_2$ | 1 | 109 |
| MgSO$_4$ | 1 | 97 |
| FeSO$_4$ | 0.1 | 100 |
| SrCl$_2$ | 1 | 94 |
| ZnCl$_2$ | 1 | 103 |
| MnCl$_2$ | 1 | 106 |
| BaCl$_2$ | 0.1 | 87 |
| CoCl$_2$ | 1 | 104 |
| K C N | 0.2 | 79 (0)* |
| CuSO$_4$ | 0.1 | 20 |
| HgCl$_2$ | 0.1 | 0 |
| p-Chloromercuriphenyl-sulfonic acid | 0.1 | 0 |
| α, α'-Dipyridyl | 1 | 85 |
| O—Phenanthroline | 1 | 103 |
| Salicylaldoxime | 1 | 91 |
| Hydroxylamine | 1 | 110 |
| Antimycin A | 2 × 10$^{-3}$ | 94 (38)* |

*aldehyde oxidase of animal origin for comparison purposes.

(4) Molecular weight

The present enzyme has a molecular weight of about 110,000, as measured by a gel filtration method using Sephacryl S-300 Super Pine (product of Pharmacia Fine Chemicals Inc., Sweden).

(5) Uniformity

Ultracentrifuge image of the present enzyme (maximum revolution: 55,430 rpm) shows a single precipitation pattern.

A comparison of the present enzyme with the known aldehyde oxidase of animal origin reveals that: (1) the aldehyde oxidase of animal origin acts upon a wide range of substrates such as various nitrogen-containing aromatic heterocyclic compounds, purine, hypoxanthine and quinines, whereas the present enzyme has a specific action upon aldehydes, and no action upon other nitrogen-containing compounds; and (2) the known aldehyde oxidase is strongly inhibited by antimycin A and KCN, whereas the present enzyme is not strongly inhibited.

The present enzyme is produced by culturing a microorganism belonging to the genus Pseudomonas, Bacillus, Microbacterium, Escherichia, Bdellovibrio, Cytophaga or Sporolactobacillus which has the ability to produce such enzyme and thereafter recovering the enzyme by known techniques. Preferred microorganisms are identified below.

|  |  | Page No. |
| --- | --- | --- |
| *Pseudomonas stutzeri* | IFO 12695 | 225-6 |
| *Pseudomonas pavonacea* | IAM 1512, ATCC 951 | 238 |
| Pseudomonas sp No. 6233 | FERM P-6467 |  |
| *Bacillus subtilis* | FERM P-6468 | 531-3 |
| *Bacillus circulans* |  | 539 |
| *Bacillus bodenheimer* |  |  |
| *Escherichia coli* | IAM 1264, ATCC 10798 | 293-6 |
| *Corynebacterium glycinophilum* | ATCC 21341 |  |
| *Corynebacterium glutamicum* | ATCC 13032 | 617 |
| *Microbacterium lacticum* | ATCC 8180, FERM P-1406 | 628-9 |
| *Bdellovibrio bacteriovorus* | ATCC 15364 | 212-4 |
| *Cytophaga dissalvens* var. *nigrescens* | ATCC 21048 |  |
| *Cytophaga dissalvens* | ATCC 21287 |  |
| *Sporolactobacillus inulinus* | ATCC 14897 | 550-1 |

The page numbers identified above correspond to those pages of Bergey's Manual of Determinative Bacteriology, 8th edition, where the microbiological description is given.

The strain No 6233 identified as Pseudomonas sp is a novel strain isolated by the present inventors, and its microbiological properties and basis for its identification are described below. The tests for identification were carried out according to the procedures of "Classification and Identification of Microorganisms" compiled by Takeji Hasegawa and published by Gakkai Shuppan Center (1975). As the basis for classification and identification, reference was made to Bergey's Manual, 8th edition (1974) and R. Y. Stanier, et al.: The Aerobic Pseudomonas: The Taxonomic Study, J. Gen. Microbiol., 43; 159-271, (1966).

I. Microbiological properties

A. Morphological characteristics of cells

Cells of the 6233 strain cultured on a bouillon agar medium at 30° C. for 24 hours are characterized by: rods, $(0.7-0.8\mu) \times (2.0-3.0\mu)$, mainly single, rarely in pairs, motile with polar monotrichous flagellation. Gram-negative and asporic. Presence of poly-$\beta$-hydroxybutyric acid granules is observable in the cells.

B. Culture characteristics

1. Culturing on a bouillon agar plate medium at 30° C. for 48 hours: circular, 2-3 mm in diameter, raised with smooth and lustrous surface, entire colony rim and amorphous, opaque, yellow colony. No formation of soluble pigment.
2. Culturing on a bouillon agar slant medium at 30° C. for 24 hours: filiform with abundant growth and yellow butyrous colony.
3. Stab culturing on a bouillon agar medium at 30° C. for 48 hours: Growth only on surface.
4. Culturing in a liquid bouillon medium at 30° C. for 48 hours: slight turbid with compact or flocculent precipitate. No film formation
5. Culturing on a bouillon gelatin medium at 30° C.: slightly slow liquefaction of gelatin after 5th day.
6. Litmus milk: litmus is declorized but neither peptonization nor coagulation occurs.

C. Physiological properties

| 1. Temperature for growth: | 15-42° C., optimum 25-33° C. |
| --- | --- |
| 2. pH for growth: | 5.5-9.0, optimum 6.5-7.5 |
| 3. Oxygen requirement: | absolutely aerobic |
| 4. O-F test: | acid is formed from gluclose only aerobically without formation of gas |
| 5. Nitrate reduction: | negative |
| 6. Denitrogenation reaction: | negative |
| 7. MR test: | negative |
| 8. VP test: | negative |
| 9. Indol formation: | negative |
| 10. Starch hydrolysis: | negative |
| 11. Casein decomposition: | negative |
| 12. Polysaccharide formation: | negative |
| 13. Oxidase: | negative |
| 14. Urease: | weakly positive |
| 15. Catalase: | positive |
| 16. Cellulase: | negative |
| 17. Arginine dehydrase: | negative |
| 18. Lysine decarboxylase: | positive |
| 19. Ornithine decarboxylase: | negative |
| 20. Egg yolk test: | negative |
| 21. Resistance to sodium chloride: | growable at 3% and non-growable at 7% |
| 22. Resistance to 0.1% triphenyltetrazolium chloride: | yes |
| 23. Nutrient requirement: | none |
| 24. Acid formation from carbohydrate: | |

Positive: glucose, fructose, L-arabinose, and trehalose
Weakly positive: xylose, glalctose, maltose, lactose, and inositol
Negative: sucrose, cellobiose, melibiose, raffinose, glycerin, mannitol, sorbitol, dulcitol, and palicin 25. Assimilability of carbon compounds:

Assimilable compounds: ribose, xylose, L-arabinose, glucose, fructose, maltose, trehalose, cellobiose, gluconic acid, 2-keto-gluconic acid, saccharic acid, glycerin, mannitol, inositol, acetic acid, pyruvic acid, lactic acid, citric acid, succinic acid, fumaric acid, malic acid, maronic acid, tartaric acid, glycolic acid, $\beta$-hydroxybutyric acid, p-hydroxybenzoic acid, ethanol, DL-arginine, serine, histidine, valine, asparagine, betaine, and sarcosine.
Non-assimilable compounds:
L-rhamnose, sucrose, erythritol, adonitol, ethyleneglycol, propyleneglycol, levulinic acid, m-hydroxybenzoic acid, methanol, geraniol, $\beta$-alanine, acetaldehyde (0.1%) and paraldehyde (0.2%).

II. Basis for identification

The 6233 strain is identified as a strain belonging to the genus Pseudomonal from the following properties:

Gram-negative, asporic bacillus; motile with monotrichous flagella; absolutely aerotic; acid formation from glucose and no gas formation; catalase-positive; negative in indol formation, MR test and VP test; assimilating many carbon compounds; no nutrient requirement; no growth at pH 4.5 and growth at 37° C.; and G-C ratio of DNA is 63.8% by mole.

Microorganisms of the genus Pseudomonas are generally oxidase-positive, but contain a few oxidase-negative species or strains. Bergey's Manual describes 29 species of the genus Pseudomonas. Among these 29 species, two, namely, *Pseudomonas cepacia* and *Pseudomonas marginata,* were selected based upon the description given, as strains relatively close to the 6233 strain. *Pseudomonas stutzeri* disclosed herein as a microorganism capable of producing aldehyde oxidase and its analogous species, yellow *Pseudomonas mendocina* were also selected as similar to the 6233 strain. The differences in microbiological properties between the four strains and strain No. 6233 are set forth in Table 3.

*P. stutzeri* and *P. mendocina* are identical with No. 6233 in G-C ratio and number of flagella and further in having a yellow pigment as to the latter, but have differences in denitrogenation reaction, and reactions to oxidase and arginine dehydrase and also considerable differences in assimilability of carbon compounds.

*Pseudomonas pavonacea* which also identified herein as a suit strain for producing the present enzyme, is only mentioned by species name in Bergey's Manual, 7th edition (page 105), this species is described; and from such description it is different in the following respects from No. 6233:

1. Cells: $0.5\mu \times 4.5\mu$, single or in chain
2. Colony: green
3. Medium shows a brown color.
4. Viscous precipitates are formed by liquid culturing.
5. No acid formation from glucose
6. Generally aerobic
7. Optimum growth temperature: 27° C., poor growth at 37° C.

From the foregoing comparisons, the strain No. 6233 is identified as a novel strain of the genus Pseudomonas which does not belong to any of 29 species disclosed in Bergey's Manual, 8th edition, or those additional species.

The 6233 strain has been deposited with the Fermentation Research Institute, Agency of Industrial Science and Technology as Pseudomonas sp No. 6233 FERM

TABLE 3

| | No. 6233 | P. cepacia | P. marginata | P. stutzeri | P. mendocina |
|---|---|---|---|---|---|
| G - C% | 63.8 | 67–68 | 68.5 | 60.7–64.3 | 62.8–64.3 |
| Flagella | 1 | >1 | >1 | 1 | 1 |
| Color | yellow | yellow or green | yellowish green | pale reddish brown | yellow |
| Oxidase | − | + | d | + | + |
| Starch hydrolysis | − | − | − | + | − |
| Gelatin liquefaction | + | d | + | − | − |
| Denitrogenation reaction | − | − | − | + | + |
| Arginine dehydrase | − | − | − | + | + |
| Assimilability | | | | | |
| ribose | + | + | + | −* | |
| xylose | + | + | + | − | − |
| L-arabinose | + | + | +* | − | − |
| maltose | + | + | − | + | − |
| trehalose | + | + | +* | − | − |
| sucrose | − | + | + | −, +* | +* |
| 2-ketogluconic acid | + | + | d | − | − |
| adonitol | − | + | + | −* | |
| mannitol | + | + | +* | −, +* | − |
| inositol | + | + | +* | − | − |
| ethyleneglycol | − | −* | −* | + | + |
| propyleneglycol | − | −* | ±* | + | + |
| levulinic acid | − | + | − | − | + |
| m-hydroxybenzoic acid | − | + | − | − | |
| geraniol | − | − | − | − | + |
| β-alanine | − | + | ±* | − | + |
| histidine | + | + | + | − | + |
| valine | + | d | + | + | + |
| sarcocine | + | + | + | − | + |

Note:
+ more than 90% positive strains
± weakly positive
d 10–90% positive strains
− more than 90% negative strains
*test data As is apparent from the foregoing Table, *P. marginata* is similar to No. 6233 in many respects including the reaction to oxidase, but is different in G-C ratio and number of flagella regarded as basic properties of the species. *P. cepacia* is also quite similar, but is oxidase-positive and different in G-C ratio and number of flagella.

P-6467. In a biologically pure culture, the strain is characterized as capable of producing, when cultured, aldehyde oxidase in recoverable quantities.

For the culturing step, either a synthetic or natural medium may be used as long as it contains an appropriate carbon source, nitrogen source, inorganic materials and other nutrients required by the particular microorganism employed. As the carbon source, saccharides such as glucose, sucrose, soluble starch, molasses, etc. and sugar alcohols such as glycerol, sorbitol, mannitol and the like may be used. As the nitrogen source, aqueous ammonia, various inorganic and organic ammonuim compounds such as ammonium chloride, ammonium sulfate, ammonium carbonate, ammonium acetate, ammonium phosphate, etc.; nitrogen compounds such as urea, etc.; nitrogeneous organic materials such as peptone, yeast extract, casein hydrolyzate, defatted soybean and its liquefied product and the like may be used. As inorganic materials, salts of such metals as sodium, potassium, manganese, magnesium, calcium, cobalt, nickel, zinc, copper, etc., and salts of chromium, sulfuric acid, phosphoric acid, nitric acid, hydrochloric acid and the like are appropriate.

The yield of aldehyde oxidase can be enhanced by adding sarcocin, betaine, dimethylglycine, choline, betaine aldehyde, trimethylamine, ethyl alcohol, methyl alcohol and the like to the culture medium either alone or in combination as an enzyme inducer. Similarly, materials containing these compounds may be used.

Culturing is usually carried out at a temperature in the range of 15° to 45° C., preferably 28° to 35° C., and at a pH of 6.0 to 8.5, preferably 6.5 to 8.0. After shaking culture or submerged stirring culture under these conditions for 20 to 30 hours, a significant amount of aldehyde oxidase is produced in a culture liquor and/or in the microbial cells, and may be recovered therefrom.

Since the aldehyde oxidase is usually formed in the microbial cells, a suitable procedure for recovering the enzyme from the cells is described below.

After completion of culturing, the cells obtained by centrifugation of the culture liquor, are thoroughly washed with water or a buffer solution. Then, the washed cells are suspended in an appropriate amount of a buffer solution and disrupted mechanically, for example, by means of a mortar, Dynomill, Manton-Gaulin, French press, Fuse press or ultrasonic disintegrator. Solid materials are removed from the thus obtained disrupted cell suspension by centrifugation or filtration, and then the aldehyde oxidase is recovered from the suspension according to the conventional procedure for isolating enzymes. For example, the enzyme can be obtained as a powder by: (1) fractional precipitation with ammonium sulfate; (2) column chromatography on DEAE-cellulose; (3) sieve fractionation by Sephadex; (4) column chromatography on hydroxyapatite; and (5) freeze-drying of active fractions. Of course, repetition of these procedures, and combinations thereof with any other conventional purification methods can be used if necessary.

The enzyme accumulated in the culture liquor can be recovered in the same manner as above except that the steps of isolation and disruption of the cells are omitted.

Certain specific embodiments of the invention are illustrated by the following representative examples.

EXAMPLE 1

In this example, Pseudomonas sp No. 6233 was inoculated in 14 2 l-Erlenmeyer flasks each containing 0.3 l of a medium consisting of a 2 g/dl creatinine, 0.1 g/dl $(NH_4)_2SO_4$, 0.05 g/dl $K_2HPO_4$, 0.05 g/dl $MgSO_4$, 0.02 g/dl KCl, 0.2 g/dl yeast extract, 0.1 g/dl malt extract, and 0.3 g/dl peptone (pH 7.0) and cultured with aeration and stirring at 28° C. for 24 hours. 4.2 l of the thus obtained culture liquor was treated in a continuous centrifuge to recover about 20 g of cells. The cells were suspended in 0.84 l of a 0.05M phosphate buffer solution (pH 7.0) and disrupted in a mill (Dyno mill KD-L made by Willy A. Bachofen).

Then, the disrupted cell suspension was centrifuged in a freeze centrifuge ($11,000 \times g$; 20 minutes) to recover a supernatant. Fractions of the supernatant obtained by precipitation with 0-80% saturated ammonium sulfate were dissolved in 95 ml of 0.01M phosphate buffer solution (pH 7.0) The solution was dialyzed against 40 l of the same buffer solution using a cellophane tube as a dialysis membrane for 24 hours, while exchanging the dialysis solution every 8 hours. The activity yield of the dialyzate was 95%.

Then, the dialyzate was kept at 70° C. for 30 minutes and the precipitates thus formed were removed by centrifugation ($11,000 \times g$: 20 minutes). The activity recovery of the supernatant was 100%.

Then, ammonium sulfate was added to the supernatant and the fractions obtained by precipitation with 30-60% saturated ammonium sulfate were collected and dissolved in 9.4 ml of 0.01M phosphate buffer solution (pH 7.0). The solution was dialyzed against 16 l of the same buffer solution using a cellophane tube as a dialysis membrane for 24 hours, while exchanging the dialysis solution every 12 hours. The activity recovery of the dialyzate was 50%.

The dialyzed enzyme solution was passed through a column containing 100 ml of hydroxyapatite equilibrated in advance with 0.01M phosphate buffer solution (pH 7.0), whereby aldehyde oxidase was adsorbed. Impure protein was washed off with the same buffer solution.

Then, phosphate buffer solutions (pH 7.0) with concentration gradient of 0.01M to 0.4M were passed through the column, and the eluates were fractionally recovered. Fractions with a high specific activity were collected and 70% saturated ammonium sulfate was added to form precipitates. The precipitates were recovered by centrifugation ($11,000 \times g$; 20 minutes) and dissolved in 1.5 ml of 0.01M phosphate buffer solution (pH 7.0). The resulting solution was dialyzed against the same buffer solution using a cellophane tube as a dialysis membrane. The activity recovery of the dialyzate was about 10%.

Then, the thus obtained supernatant was passed through a column containing 230 ml of Sephadex G-150 (made by Pharmacia Fine Chemicals) equilibrated in advance with 0.05M phosphate buffer solution (pH 7.0) containing 0.1M NaCl, and the eluates were fractionated by passing the same buffer solution through the column.

As a result, the active fractions were eluted as a single peak. Fractions with a high specific activity were collected and concentrated with a collodion bag (made by Saltrius), whereby 2.3 mg of a purified enzyme preparation of aldehyde oxidase (specific activity: 2.88 U/mg) was obtained.

Total activity yield was 2.2%, and the specific activity amounted to 100 times higher.

EXAMPLE 2

In this example, each of the strains shown in Table 4 was inoculated in a 2l-Erlenmeyer flask containing 300 ml of a medium having the same composition as in Example 1, and cultured with shaking at 30° C. for 24 hours. Each culture liquor was then treated by freeze centrifuge ($11,000 \times g$; 20 minutes) to collect cells. About 1 g of the cells was suspended in 10 ml of 0.01M phosphate buffer solution (pH 7.0) and subjected to ultrasonic treatment in an ultrasonic disintegrator for 20 minutes, followed by freeze centrifugation (20,000×g; 20 minutes) to obtain a supernatant. The aldehyde oxidase activity of the thus obtained supernatants was measured, and the results are shown in Table 4.

TABLE 4

| Strain | | aldehyde oxidase activity (units/ml culture product) |
|---|---|---|
| Pseudomonas stutzeri | IFO 12695 | 26 |
| Pseudomonas pavonacea | IAM 1512, ATCC 951 | 33 |
| Pseudomonas sp No. 6233 | FERM P-6467 | 24 |
| Bacillus subtilis | FERM P-6468 | 3 |
| Bacillus circulans | | 1 |
| Bacillus bodenheimer | | 3 |
| Escherichia coli | IAM 1264, ATCC 10798 | 5 |
| Corynebacterium glycinophilum | ATCC 21341 | 7 |
| Corynebacterium glutamicum | ATCC 13032 | 7 |
| Microbacterium lacticum | ATCC 8180, FERM P-1406 | 6 |
| Bdellovibrio bacteriovorus | ATCC 15364 | 8 |
| Cytophaga dissalvens var. nigrescens | ATCC 21048 | 10 |
| Cytophaga dissalvens | ATCC 21287 | 10 |
| Sporolactobacillus inulinus | ATCC 14897 | 17 |

What is claimed is:

1. Aldehyde oxidase characterized by: a molecular weight of about 110,000, an optimum pH of about 6.5 and an optimum temperature of about 50° C., wherein the oxidase catalyzes the oxidation reaction of an aldehyde to a corresponding acid and does not exhibit substrate activity to the group of compounds including N'-methylnicotinamide, quinoline, purine, hepoxanthine and quinine.

2. A process for producing the aldehyde oxidase defined in claim 1 which comprises culturing an aldehyde oxidase producing microorganism belonging to the genus Pseudomonas, Bacillus, Microbacterium, Escherichia, Bdellovibrio, Cytophaga or Sprorolactobacillus in a nutrient medium until recoverable amounts of the enzyme is accumulated and thereafter recovering the enzyme therefrom.

3. A process according to claim 2 wherein said microorganism belongs to the species, *Pseudomonas stutzeri, Pseudomonas pavonacea,* Pseudomonas sp. No. 6233, *Bacillus subtilis, Bacillus circulans, Bacillus bodenheimer, Escherichia coli, Corynebacterium glycinophilum, Corynebacterium glutamicum, Microbacterium lacticum, Bdellovibrio bacteriovorus, Cytophaga dissalvens* or *sporolactobacillus inulinus.*

4. A process according to claim 2 wherein said culturing is carried out at a temperature of about 28° to 35° C. and a pH of about 6.5 to 8.0.

5. A process according to claim 2 wherein said medium includes at least one enzyme inducer selected from the group consisting of sarcocin, betaine, dimethylglycine, choline, betaine aldehyde, trimethyamine, ethyl alcohol and methol alcohol.

6. A biologically pure culture of the microorganism Pseudomonas sp. No. 6233, FERM P-6467, which produces recoverable quantities of aldehyde oxidase when cultured.

* * * * *

UNITED STATES PATENT AND TRADEMARK OFFICE
CERTIFICATE OF CORRECTION

PATENT NO.  : 4,666,842
DATED       : May 19, 1987
INVENTOR(S) : TAKAYUKI UWAJIMA, ET AL.

It is certified that error appears in the above-identified patent and that said Letters Patent is hereby corrected as shown below:

Column 7, at line 4, insert:  --D. G-C content of DNA: 63.8% by mole--

Column 7, line 8, "Pseudomonal" should read --Pseudomonas--

Column 8, line 7, after "which" insert --is--

Column 8, line 9, after "Manual," insert --8th edition. However, in Bergey's Manual, 7th--

Column 12, line 8, "Sprorolac-" should read --Sporolac--.

Signed and Sealed this

Twenty-second Day of September, 1987

Attest:

DONALD J. QUIGG

Attesting Officer    Commissioner of Patents and Trademarks